United States Patent [19]

Groleau et al.

[11] Patent Number: 5,434,062
[45] Date of Patent: Jul. 18, 1995

[54] PROCESS FOR THE PREPARATION OF POLY-BETA-HYDROXYBUTYRIC ACID POLYMERS

[75] Inventors: Denis Groleau, Laval; Denis Bourque, Montreal; Yves Pomerleau, Beaconsfield, all of Canada

[73] Assignee: National Research Council of Canada, Ottawa, Canada

[21] Appl. No.: 185,101

[22] Filed: Jan. 21, 1994

Related U.S. Application Data

[62] Division of Ser. No. 980,081, Nov. 23, 1992, Pat. No. 5,302,525.

[51] Int. Cl.$^6$ .......................... C12N 1/12; C12P 7/40
[52] U.S. Cl. .................... 435/135; 435/252.1; 435/872
[58] Field of Search ............... 435/135, 252.1; 975/822

[56] References Cited

PUBLICATIONS

Bourque et al "Appl. Microbiol. Biotechnol." vol. 37 pp. 7–12 (Apr. 1992).

*Primary Examiner*—Herbert J. Lilling
*Attorney, Agent, or Firm*—Ronald S. Kosie; Robert Brouillette

[57] ABSTRACT

The present invention relates to a type of polymer comprising repeating units of formula

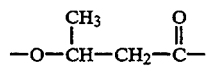

and in particular to a poly-$\beta$-hydroxybutyrate polyester type polymer. The present invention also relates to a microbiological process for the production of the above type of polymer, to a methylotrophic microorganism (bacterium) for use in such a process, and to means for controlling such bioprocesses.

19 Claims, No Drawings

PROCESS FOR THE PREPARATION OF POLY-BETA-HYDROXYBUTYRIC ACID POLYMERS

This is a divisional application of application Ser. No. 07/980,081 filed on Nov. 23, 1992, now U.S. Pat. No. 5,302,525.

The present invention relates to a type of polymer comprising repeating units of formula

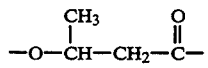

in particular to a poly-β-hydroxybutyrate polyester type polymer. This type of polymer is sometimes hereinafter referred to simply as PHB. The present invention also relates to a microbiological process for the production of PHB, to a methylotrophic microorganism (bacterium) for use in such a process, and to means for controlling such bioprocesses.

The polymers of poly-β-hydroxybutyrate type have attracted considerable interest since this type of polymer is a biodegradable thermoplastic material; see for example Canadian patent no. 1,098,463 the entire contents of which are incorporated herein by reference.

Poly-β-hydroxybutyrate type polymers are accumulated by various microorganisms as an energy reserve material and are stored as granules within the microbial cell. Poly-β-hydroxybutyrate type polymers extracted from such cells have as mentioned above a repeating unit the structure of which has the following general formula:

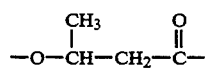

Many species of bacteria are known which will, under certain conditions, produce PHB (see, for example, European patent application no. 80300432.4, Canadian patent no. 1,223,687, U.S. Pat. No. 4,477,654 (the entire contents of this European application, the Canadian patent and the American patent are incorporated herein by reference); see also "Polyhydroxybutyrate: an Intriguing Biopolymer", Edwin A Dawes, Bioscience Reports, Vol. 8, no. 6, (1988) 537–546, "A Survey of the Accumulation of novel Polyhydroxyalkanoates by bacteria", G. W. Haywood, et al, Biotechnology Letters, Vol. 11, no. 7,471–476 (1989)).

U.S. Pat. No. 4,477,654 (the entire contents of which are, as mentioned above, incorporated herein by reference), for example, relates to a microbiological process for the preparation of poly-β-hydroxybutyrate type polymers which contain other types of repeating units in addition to the repeating unit mentioned above. The number of repeating units in the polymer chain will of course dictate the molecular weight of the polymer. This U.S. patent also teaches that for the microorganism(s) mentioned therein, PHB accumulation may be facilitated or favoured by conducting at least part of the cultivation under conditions of limitation of an essential requirement for growth or reproduction but not for the accumulation of polyester. The patent indicates that the most convenient growth requirement limitation is a limitation of assimilable nitrogen; in this case the substrate is preferably nitrogen free.

The use of methanol as a (i.e. nitrogen free) substrate for the production of poly-β-hydroxybutyrate type polymers has attracted interest since methanol is a relatively cheap source of carbon.

Certain species of bacteria known as the methylotrophic group of bacteria, may use methanol as a carbon substrate for the production of PHB (see for example, "Mass production of poly-β-hydroxybutyric acid by fully automatic fed-batch culture of methylotroph", Takahiro Suzuki, et al, Applied Microbiology Biotechnology (1986) 23:322–329; "Kinetics and effect of nitrogen source feeding on the production of poly-β-hydroxybutyric acid by fed-batch culture", Takahiro Suzuki, et al, Applied Microbiology and Biotechnology (1986) 24:366–369; "Mass production of poly-β-hydroxybutyric acid by fed-batch culture with controlled carbon/nitrogen feeding", Takahiro Suzuki, et al, Applied Microbiology and Biotechnology (1986) 24:370–374; "Control of molecular weight of poly-β-hydroxybutyric acid produced in fed-batch culture of *Protomonas extorguens*", Takahiro Suzuki, et al, Applied Microbiology and Biotechnology (1988) 27:487–491; "Studies on the growth-associated accumulation of poly-β-hydroxybutyric acid with *Methylobacterium rhodesianum Z*", U. Hilger, et al. Zentalblo Mikrobiol (1991), 146:83–88; "Optimization of growth medium and poly-β-hydroxybutyric acid production from methanol in *Methylobacterium organophilum*", Choi, Joon H., et al, Kor J. Appl. Microbiol. Bioeng. Vol 17, no. 4, 392–396 (1989); "Production of poly-β-hydroxybutyric acid by methanol assimilating bacterium, *Pseudomonas* sp. ILS-003" Il-Seok Lee and Won-Gi Bang, J. Korean Agric. Chem. Soc. 34(3):273–278 (1991); see as well Canadian patent nos 1,100,896 and 1,239,361 for other examples of fermentation processes using methanol as a carbon substrate).

Generally speaking, however, there is a continuing demand to provide (alternate) bioprocesses which exploit microorganisms which give high PHB yields of high quality and for which methanol may, for example, be used as a carbon substrate.

The present invention in accordance with a one aspect provides for a biologically purified culture of a *Methylobacterium extorguens* microorganism strain designated by the ATTC no. 55366 and mutants and variants thereof.

The ATCC number 55366 is the number designated to the purified specimen culture deposited on October 14, 1992 with the American Type Culture Collection (ATCC, 12301 Parklawn Drive, Rockville, Md. 20852, United States of America).

In accordance with another aspect, the present invention provides for a method of producing a polymer comprising repeating units of formula

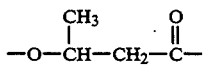

method comprising aerobically culturing a purified *Methylobacterium extorguens* microorganism strain designated by the ATTC no. 55366 and mutants and variants thereof whereby said polymer is accumulated in said microorganism.

The microorganism strain of the present invention is, for example, able to metabolize methanol for the purpose of producing a PHB material. The present invention, however, also embraces the cultivation of the new microorganism strain, under aerobic culture conditions, for metabolizing other carbon sources for the purpose of producing a PHB material. The substrate may, for example, be selected from materials such as listed below and which include ethanol and organic acids.

The microorganism strain of the present invention is capable of accumulating (some) PHB while growth of the microorganism is taking place. However, the accumulation of PHB is favoured or enhanced if one or more of the essential requirements for reproduction of the microorganism is limited (e.g. is exhausted or is in sub-optimal concentrations). For example, when aerobically cultivated on a suitable substrate (i.e. a suitable source of energy and carbon) in batch culture, the microorganism strain of the present invention will reproduce until one or more essential requirements for reproduction becomes limiting or is exhausted; thereafter providing that the substrate is not exhausted, the microorganism will accumulate (substantial) PHB. Accordingly, the expression "starvation condition" shall be understood herein as characterising cultivation as being carried out under a condition of limitation of at least one requirement essential for growth or reproduction but not for the accumulation of polyester, e.g. a nutrient depleted over time is not augmented in the culture medium.

The present invention is, in particular, concerned with the use of the microorganism strain of the present invention to metabolize methanol for the purpose of producing PHB including derivatives thereof and analogous materials.

Thus, in accordance with a further aspect the present invention provides for a method of producing a polyester comprising repeating units of formula

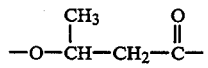

method comprising aerobically culturing a microorganism, capable of accumulating said polyester, in an aqueous medium on an assimilable carbon source consisting of methanol, with at least part of the cultivation being conducted under a starvation condition whereby one or more essential requirements for microbial growth is limited and whereby said polyester is accumulated in said microorganism, characterized in that said microorganism consists of a purified *Methylobacterium extorguens* microorganism strain designated by the ATTC no. 55366 and mutants and variants thereof.

In accordance with the present invention, a convenient growth requirement limitation, for example, is a limitation of assimilable nitrogen. Although deliberate nitrogen limitation is not necessary to initiate some PHB accumulation, deliberate nitrogen limitation enhances PHB accumulation once the desired cell density has been reached.

In accordance with the present invention, a method as described herein may include the step of recovering the polyester from the microorganism.

It is to be understood herein, that if a "range", "group of substances" or the like is mentioned with respect to a particular characteristic of the present invention, the present invention relates to and explicitly incorporates herein each and every specific member and each and every combination of sub-ranges (or sub-groups, etc.) therein, whatsoever. Thus, any specified range (or group, etc.) is to be understood as a shorthand way of specifically referring to each and every member of a range (or group) individually as well as each and every possible sub-ranges (or sub-groups, etc.) encompassed therein. For example, with respect to the concentration of any component (e.g. the concentration of methanol), the mention of the range of 0.01 to 12 g/l is to be understood as specifically incorporating herein each and every individual concentration as well as sub-range, such as for example 1.7 g/l, 1.0 g/l, 2.0 to 5 g/l, etc.; similarly with respect to ranges/groups for temperature, pressure, nutrients, molecular mass, rpm etc...

The strain of methylotrophic bacterium of the present invention identified as *Methylobacterium extorguens* ATCC number 55366 is able to accumulate significant quantities of PHB (e.g. about 40% to 50% of the cell weight on a dry weight basis) from the aerobic metabolism, for example, of methanol in a minimal culture medium. An example of a minimal culture medium is Medium 784 as described by the American Type Culture Collection and which is referred to below. A (methanol) fermentation process based on this microorganism may provide for very high cell densities and significant accumulation of high molecular weight PHB.

The above mentioned strain of *Methylobacterium extorguens* of the present invention, was isolated from a soil sample regularly contaminated with used oil products for at least 40 years; the soil sample originated from the region of Quebec (Canada). The strain has a pink pigmentation and is a Gram-negative, sometimes motile, rod (coccobacillus-to-rod shape). The pink pigment(s) is(are) not soluble in water and no evidence of pigment liberation in older cultures has been found yet. The bacterium strain is also catalase-positive and oxidase-positive, and contains the enzyme hydroxypyruvate reductase indicating that carbon assimilation by this bacterium is done via the serine pathway. The fatty acid profile of this culture was determined by gas chromatography and gave a similarity index of 0.627 with known strains of *Methylobacterium extorguens* indicating an excellent match (analysis was carried out by MICROCHECK INC., Northfield, Vt. 05663, U.S.A.). Using appropriate growth conditions (e.g. a starvation condition), the cells, after cultivation, contain granules of poly-β-hydroxybutyrate type polymer (PHB) which may be detected in known manner such as, for example, by phase contrast microscopy or chemical analysis (for instance by a gas chromatographic method as described by Braunegg et al Eur. *J. Appl. Microbiol. Biotechnol.* 6:29–37 (1978) and Bourque et al Appl. Microbiol. Biotechnol. 37:7–12 (1992)).

The above mentioned strain of *Methylobacterium extorguens* of the present invention, does not use glucose, lactose, or sucrose as a carbon source under (known) aerobic conditions, i.e. when tested in shake flask experiments with (very) good agitation conditions as a means for providing sufficient aeration. Biochemical tests carried out using BIOLOG (R) plates (from BIOLOG INC. Hayward, Calif. 94545, U.S.A.) indicated that the new strain is a poor utilizer of sugars but is mainly an organic acid utilizer; for instance, formic acid, β-hydroxybutyric acid, D,L-lactic acid, malonic acid, propionic acid, and succinic acid all sustained growth of this bacterium. The above mentioned strain of *Methylobacterium extorguens* of the present invention does, however, make use of ethanol to a certain extent. Limited growth but appreciable poly-β-hydroxybutyrate production was observed when ethanol was the only carbon source available and a minimal culture medium (such as described herein) was used.

The above mentioned strain of *Methylobacterium extorguens* of the present invention, grows well in a minimal aqueous culture medium (see Medium 784 in Table 2 mentioned below) containing an appropriate mineral component(s) and which additionally contains methanol as the only carbon source.

The bacterium also grows well on methanol agar plates containing Medium 784 plus agar; using this medium, or modifications of this medium, pink colonies are easily seen after growth for about 3 days at 28° to 30° C. The bacterium also grows well in Medium 784 containing methanol and a complex nitrogen source such as HySoy, a hydrolysate of soybean protein. The bacterium grows well on Nutrient Agar plates but poorly on Trypticase Soy Agar plates.

The bacterium grows well at 28° to 32° C. in media with an initial pH of 6 to 7. When growth is carried out in liquid media, the bacterium remains pink-pigmented and shows no sign of slime production. The intensity of the pink coloration however varies with growth conditions and culture medium, especially with the mineral composition of the medium. Growth of the bacterium in a minimal medium containing only methanol as carbon source leads to acidification of the medium; this acidification may be neutralized by addition of ammonium hydroxide, sodium hydroxide, or potassium hydroxide (or any other acceptable alkaline solution).

In order to favour a (desired) high cell density culture and high PHB accumulation, the mineral composition of the culture medium preferably is such as to support the desired growth rate and to sustain the microorganism. For example, in order to obtain optimal growth of the microorganism, and also for reaching maximal growth rate, the needs of the microorganism strain of the present invention with respect to the levels of all pertinent necessary mineral elements should be met. In accordance with the present invention, a mineral is considered to be pertinent when its presence in the culture medium has a beneficial effect on cell biomass production and/or growth rate. The influence of each mineral ion or mineral solution may be determined empirically by measuring the effect of various concentration of the mineral or mineral solution on the rapidity of growth (growth rate) and cell biomass production (amount of cell biomass produced per unit of mineral (mineral solution) present or consumed). The effect of the absence of a mineral (mineral solution) may be determined in an analogous manner. Thus, for example, although the minerals listed in Table 1 below are beneficial for growth, some of them are more beneficial than others, particularly manganese, magnesium, calcium, iron, sulphate, and ammonium ions. In any event, for example, sufficient amounts of ions such as manganese, magnesium, calcium, iron, zinc, sulphate, ammonium, and phosphate ions, should be present in order to reach high cell density culture and consequently high PHB levels. The Medium 784 as described by the American Type Culture Collection (see Table 2 below) is an example of a suitable (minimal) culture medium.

A (minimal) aqueous (nutrient) medium may, for example, comprise the components (in the specified amounts) as set out in Table 1 below:

TABLE 1

| Component | Amount |
| --- | --- |
| NH$_4$Cl | from 0 to 2.5 g/L |

TABLE 1-continued

| Component | Amount |
| --- | --- |
| (NH$_4$)$_2$SO$_4$ | from 0 to 3.0 g/L |
| KH$_2$PO$_4$ | from 0.27 to 2.61 g/L |
| K$_2$HPO$_4$ | from 0 to 2.1 g/L |
| Na$_2$HPO$_4$.7H$_2$O | from 0 to 8 g/L |
| MgSO$_4$.7H$_2$O | from 0.22 to 2.7 g/L |
| CaCl$_2$.2H$_2$O | from 1.5 mg to 0.6 g/L |
| FeSO$_4$.7H$_2$O | from 1 mg to 240 mg/L |
| MnCl$_2$.4H$_2$O | from 0 to 0.2 mg/L |
| MnSO$_4$.H$_2$O | from 0 to 100 mg/L |
| ZnSO$_4$.7H$_2$O | from 0 to 30 mg/L |
| CuCl$_2$.2H$_2$O | from 0 to 0.1 mg/L |
| CuSO$_4$.5H$_2$O | from 0 to 20 mg/L |
| NiCl$_2$.6H$_2$O | from 0 to 0.1 mg/L |
| Na$_2$MoO$_4$.2H$_2$O | from 0.02 to 10 mg/L |
| CoCl$_2$.6H$_2$O | from 0.02 to 10 mg/L |
| H$_3$BO$_3$ | from 0.015 to 5 mg/L |
| Methanol[1] | from 0.01 g/L to 12 g/L |

[1]Or any other consumable carbon (and energy) source.

As previously mentioned Medium 784 as described by the American Type Culture Collection is an example of a suitable minimal culture medium. The composition of Medium 784 may, however, be varied in any desired fashion keeping in mind that the composition of the culture medium is to be such as to facilitate cell growth and in particular the production of PHB by the microorganism strain of the present invention. Other minimal culture media may also be used keeping the above in mind. Examples of such other media are shown in Table 2 below.

TABLE 2

Composition (per liter) of example minimal aqueous media

| Elements | Medium | | | |
| --- | --- | --- | --- | --- |
| | AMS #784*[1] | Choi*[2] | A1*[3] | A2*[3] |
| NH4Cl | 0.5 g | — | — | — |
| (NH4)2 SO4 | — | 1.5 g | 1.5 g | 1.5 g |
| KH2PO4 | 0.54 g | 1.305 g | 1.305 g | 1.305 g |
| K2HPO4 | 0.7 g | — | — | — |
| Na2HPO4.7H2O | — | 4.02 g | 4.02 g | 4.02 g |
| MgSO4.7H2O | 1.0 g | 0.45 g | 0.45 g | 1.35 g |
| CaCl2.2H2O | 0.2 g | 3.3 mg | 20 mg | 60 mg |
| FeSO4.7H2O | 4.0 mg | 1.3 mg | 20 mg | 60 mg |
| MnCl2.4H2O | 30 ug | — | — | — |
| MnSO4.H2O | — | 100 ug | 4.9 mg | 14.7 mg |
| ZnSO4.7H2O | 100 ug | 130 ug | 2.6 mg | 7.8 mg |
| CuCl2.2H2O | 10 ug | — | — | — |
| CuSO4.5H2O | — | 40 ug | 800 ug | 2.4 mg |
| NiCl2.6H2O | 20 ug | — | — | — |
| Na2MoO4.2H2O | 60 ug | 40 ug | 800 ug | 2.4 mg |
| CoCl2.6H2O | 200 ug | 40 ug | 800 ug | 2.4 mg |
| H3BO3 | 300 ug | 30 ug | 600 ug | 1.8 mg |

*[1]: Ammonium mineral salts medium #784 from ATCC (ATCC 1985)
*[2]: Medium as described in Choi et al, 1989. Kor. J. Appl. Microbiol. Bioeng. 17:392–396.
*[3]: Modified version of the above referred to Choi medium as described in Choi et al, 1989. Kor. J. Appl. Microbiol. Bioeng. 17:392–396.

If the substrate used comprises methanol, the culture medium may contain various concentrations of methanol; the concentrations used, however, must be such as to facilitate the production of PHB by the microorganism strain of the present invention. Relatively low concentrations of methanol, in the order of 5 to 10 g/L, (e.g. 0.65 to 1.3 % v/v) are (partially) inhibitory or (partially) toxic to the methylotrophic bacteria of the present invention. Nevertheless, concentrations of methanol in the range of from about 2 to about 10 g/l (0.26 to 1.3% v/v) may for example be used for an aqueous culture medium. Initial concentrations of methanol up to 1.3% (v/v) may, for example, be used but growth of the bacterium may be delayed at higher concentrations; lower methanol concentrations in the range of 0.2 to 5 g/l may, if desired be used. A methanol concentration of 30 g/l has been found to completely inhibit growth.

If other types of substrates are to be used as a carbon source, the concentrations used must likewise be such as to facilitate cell growth and in particular the production of PHB by the microorganism strain of the present invention; e.g. the useful concentration ranges for ethanol, propionic acid, succinic acid, and the like may be determined empirically as for the mineral component(s) mentioned above.

In accordance with the present invention, the bacterium may first be grown in an aqueous (nutrient) medium containing sources of assimilable nitrogen, phosphorus, and other required ions, with methanol as the only carbon and energy source; thereafter culturing may for example be continued under deliberate nitrogen limitation or any other deliberate nutritional limitation for PHB production.

During the first growth phase of culturing, the microorganism grows by multiplication to give an appreciable concentration of the microorganism, as indicated by measures of cell biomass in the order of 10 to 90 gm/L (dry weight). During this phase of biomass production, methanol, for example, may be added in a fed-batch mode at a rate corresponding to the consumption rate to keep a constant methanol concentration in the culture medium; for example, at a methanol concentration of 1.6 g/l (0.21% v/v) or lower; alternatively, if desired the methanol concentration may be kept at higher values such as for example up to about 10 g/l (1.3% v/v). Other nutrients may similarly be provided to the culture medium after appropriate calculation and optimization (e.g. by empirical determination as mentioned above with respect to the mineral component(s)).

During the initial growth phase, especially when the cell density reaches values are in the 25–70 gram per liter (g/l) range (dry weight), oxygen transfer may present itself as a rate limiting factor and this limitation may force a change in the fermentation process; for example, after this point is reached, methanol may thereafter be added to the culture at a rate which is directly proportional to the amount of oxygen transferred to the liquid so that no oxygen limitation is introduced. This oxygen limitation may be determined in any suitable manner; for example when the pO2 level can no longer be maintained at an acceptable level (such as greater than 10% saturation) and tends toward zero. If needed, additional nutrients may be supplied in a fed-batch mode during this first growth phase to enhance cell biomass production; fed-batch mode refers to batch cultivation wherein one or more nutrient materials is (are) added continuously or intermittently to the batch during cultivation. During this first phase, since no known nutritional limitation is intentionally imposed, the microorganism will grow and multiply.

It is desirable to have a relatively high cell biomass at the end of the first growth phase, preferable reaching values between 20 to about 80 gm/L (dry weight); i.e. in order to obtain high PHB levels in the fermentation broth at the end of the PHB accumulation phase, it is desirable that high cell biomass concentrations be obtained at the end of the first phase.

It is not desirable that a relatively concentrated culture medium be used to achieve this goal since a concentrated culture medium may be (partially) toxic to the microorganism. The toxicity may be caused either by the high concentration of the carbon source used (methanol, ethanol, or any other carbon source) or by the high concentration of one or several ions, or by a combination of such factors. For instance, high concentrations of ammonium ions, or high concentrations of salts, may be inhibitory or toxic to the microorganism. In order to inhibit (e.g. prevent) the existence of such toxic conditions, the culture medium initially may contain acceptable levels of the nutrient(s) and thereafter during the course of the cultivation additional necessary nutrient(s) may be added continuously or intermittently to the culture medium in non-toxic or non-inhibitory amounts, e.g. the necessary nutrient(s) may be added in a fed-batch mode to the culture in response to an analysis of the culture medium composition during cultivation.

When the desired cell biomass level is reached, appreciable PHB accumulation may, as mentioned above, be initiated by setting up culture conditions in such a way that a growth requirement limitation is set in place, i.e. the first growth phase is followed by a second PHB accumulation phase wherein a starvation condition is imposed. Any means of establishing a nutritional limitation may be used keeping in mind that the purpose thereof is to facilitate PHB accumulation; examples of this are: phosphorus limitation, manganese limitation, or any other acceptable limitation.

A convenient growth requirement limitation is an assimilable nitrogen limitation. For example, ammonium hydroxide may be added during the first growth phase to maintain the pH of the culture at a desired value, and to also serve as an assimilable nitrogen source. During the subsequent enhanced PHB accumulation (i.e. second) phase the ammonium hydroxide may be replaced with potassium hydroxide (or any other non-nitrogen alkaline source); as a result of this change in alkaline solution, the microorganism will consume all of the remaining nitrogen and a nitrogen limitation will be established after some period (e.g. hours) of further metabolism.

During the second phase of enhanced PHB accumulation, an oxygen limitation may be avoided by using the same feeding strategies described earlier for the first phase of the process; e.g. by limiting the methanol feed rate in response to the amount of oxygen available to the microorganism in the culture medium.

As mentioned above, a concentrated culture medium may be toxic to the microorganism of the present invention. The toxicity may be caused by a too high concentration of the carbon source used (e.g. methanol, ethanol, or any other carbon source). For example, relatively low concentrations of methanol, in the order of 5 to 10 g/l, are (partially) inhibitory or (partially) toxic to the methylotrophic bacteria of the present invention. Accordingly, a relatively dilute methanol (culture medium) solution is preferably used for (batch) fermentation purposes (e.g. from 0.5 to less than about 5.0 g/l). If the methanol is added only at the beginning of the fermentation process, the fermentation process would require a (batch) bioreactor of relatively large size in order to obtain practical amounts of PHB at the end of the cultivation. Alternatively, a relatively small bioreactor may be used if methanol is added in a fed-batch mode in order to maintain an acceptable (e.g. non-inhibitory) methanol concentration in the culture medium in the bioreactor.

In accordance with the present invention, in order to facilitate the bioprocess, a computer may be used to regulate desired (controllable) variables during all phases of the fermentation: the biomass growth phase and the PHB production phase (with or without oxygen transfer limitation, as shall be discussed below). Any type of suitable (known) control equations may be incorporated into a computer control program for the purpose of such regulation.

For example, a computer may be used for carbon source (e.g. methanol) concentration control by adjustment of the methanol feed rate, for dissolved oxygen control by varying the agitation rate and for dissolved oxygen control by adjusting the carbon source (e.g. methanol) feed rate according to the process phase.

Thus, for fed-batch mode where methanol is used as a carbon source, the methanol concentration in the culture medium may be continuously monitored using a suitable sensor; i.e. so that the feed rate of methanol added to the bioreactor may be controlled as a function of the methanol concentration sensed by the sensor. The sensor may be operatively linked to a computer so as to provide the computer with a measured value signal (i.e. a signal corresponding to the concentration of methanol sensed by the sensor). Based upon the measured value signal, the computer, by means of any appropriate (known) algorithm, may calculate the control action required in response to the measured value signal; e.g. in response to the measured value signal, the computer may send a signal to an actuator device operatively connected to a variable speed pump for varying (or maintaining) the delivery of methanol to the bioreactor culture medium. Using such a feedback control, the methanol concentration may be maintained at (or hover about) a desired set-point value (e.g. be maintained at a methanol concentration in the culture medium used which gives the desired (e.g. maximal) growth rate). In this way the methanol concentration may, for example, be maintained at values between about 0.1 g/l to about 3 g/l or higher, if desired; for example, the methanol concentration may be maintained at 1.4 g/l for several hours or days. An appropriate control algorithm may use the measured methanol value(s) to calculate the (new) methanol feed rate and send a signal to increase or decrease the methanol feed rate as required in order to maintain the desired methanol concentration in the culture medium.

In order to facilitate such a fed-batch mode, the carbon source (e.g. methanol) concentration may be measured in the liquid phase (i.e. in the liquid culture medium); alternatively, since an oxygen containing gas is continuously or intermittently delivered to and admixed with the culture medium, the carbon source (e.g. methanol) concentration may be measured in the exhaust gas phase leaving the bioreactor.

Suitable (semi-conductor) sensors for monitoring the methanol concentration may be obtained from Figaro Eng. Inc, Wimelle, Ill., U.S.A. A Figaro TGS 822 sensor may, for example, be used to measure methanol in an exhaust gas from a bioreactor; a dissolved gas membrane probe (silicone tubing probe from Bioengineering, Switzerland) for insertion into the liquid culture medium may be used, for example, in conjunction with a Figaro TGS 812 sensor to measure methanol in the liquid phase, the sensor being able to detect and measure the concentration of methanol in a carrier gas associated with the membrane probe.

The *Methylobacterium extorguens* strain of the present invention, as mentioned earlier, is an aerobic microorganism requiring oxygen for its metabolism. The aerobic metabolism of methanol, for example, is believed to require more oxygen than the metabolism of sugars, on a molecular basis. Accordingly, during cultivation, steps should be taken to ensure that an adequate concentration of dissolved oxygen is maintained in a (liquid) culture medium, e.g. during the growth phase and during the PHB accumulation phase oxygen may be provided by oxygen transfer from a gas phase to the liquid phase.

Any suitable method may be used to feed and regulate (e.g. increase) oxygen transfer to the liquid phase. Thus, a biologically acceptable oxygen containing gas such as, for example, compressed air (or oxygen enriched compressed air and the like) may be blown (e.g. sparged) into a liquid culture medium through a tubing, the mouth of which is disposed within the body of the liquid (culture) medium. In this case, the culture medium may also be agitated by any suitable (known) agitation means; the agitation rate may be used to manipulate (e.g. increase) oxygen transfer to the liquid culture medium in order to maintain the required or desired dissolved oxygen concentration thereof.

A feed-back control system analogous to that described for methanol may be used to regulate the dissolved oxygen concentration, i.e. the dissolved oxygen concentration in the liquid medium may be monitored by a $pO_2$ (dissolved oxygen) electrode so as to provide a monitored value signal to a computer which in turn in accordance with an appropriate (known) algorithm sends a control signal to an actuator means connected to an "air" delivery device for increasing or decreasing the "air" flow and/or the agitation rate of the bioreactor system.

Any bioreactor will, however, usually have a limited capacity to transfer oxygen to aerobic microorganisms. With a fast growing microorganism and a desire for high cell density cultures, it is thus possible that the oxygen demand of the culture may exceed the maximal oxygen transfer capacity of the bioreactor. In the case of compressed air blown into an agitated liquid culture medium, the maximum capacity may, for example, be limited by the maximum agitation rate of agitator of the system being used.

However, the oxygen demand of the culture may be controlled such that the maximal oxygen transfer capacity of the bioreactor being used is not exceeded. It is possible, for example, to adjust the rate at which methanol, (or of any other carbon source), is fed to the culture medium in a fed-batch mode, as a function of the available oxygen transfer capacity of the bioreactor, i.e. methanol is added in response to the dissolved oxygen concentration in the (liquid) culture medium in lieu of being added in response to the concentration of carbon source (e.g. methanol) in the liquid culture medium. In this way, the oxygen demand required by the microorganism to metabolize the methanol may be regulated so as to not exceed the oxygen transfer capacity (i.e. the rate of oxygen transfer from the gas to the liquid medium) of the bioreactor; consequently, enough oxygen will always be available for the oxidation of the carbon source (e.g. methanol) or for PHB production. This type of feed-back control may be exploited in analogous fashion to that described above with respect to feed-back control based on methanol concentration alone.

The efficient control of any fed-batch fermentation is greatly complicated by the fact that these fermentation processes, at least during the active period of growth, occur in an nonlinear fashion with exponential increase of the control action. Open-loop control is not sufficiently precise to insure good fermentation conditions; in accordance with open-loop control a material is added to a system without consideration for the real time value of the material in the system. Nonlinear close-loop control such as described herein, has the advantage that it may take into account the nonlinearities of the process; in accordance with such closed loop control, one or more elements of the process such as, for example, methanol concentration, dissolved oxygen level, pH, etc.. is (are) adjusted based on a measured value thereof representative of the system.

In accordance with the present invention equations for fed-batch mode wherein methanol is continually (or intermittently) added to the liquid culture medium is provided which were developed from mass balance equations which include the above mentioned nonlinearities. The equations are designed in such a way that the response of the controlled variable (e.g. methanol) to the set-point value is linear in closed-loop in spite of the nonlinearities of the process and the increasing dynamics of the process as biomass concentration increases.

Accordingly, the present invention in a further aspect provides a method of producing a polymer comprising repeating units of formula

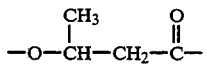

wherein a microorganism capable of accumulating said polymer (e.g. a microorganism of the present invention) is aerobically cultivated in an aqueous medium on an assimilable carbon source, said method comprising the step of adding said carbon source to the aqueous medium in accordance with one or more of the equations described below.

Thus, in accordance with the present invention, the following control equation (Ia) may be used for controlling the concentration of a carbon source (e.g. methanol) in a liquid culture medium (e.g. during the entire fermentation period or only for the initial fermentation period when the oxygen demand of the biomass does not exceed the oxygen transfer rate of the fermentation system):

$$F = V * \left[ \frac{((1/\tau_d) * (M^* - M)) + (k^1 * OTR)}{(M^i - M)} \right] \qquad \text{(Ia)}$$

wherein

F is the feed rate of the carbon source (e.g. methanol) feed stream (e.g. liters per hour)

M is the measured concentration (e.g. grams per liter) of the carbon source (e.g. methanol) in the culture medium $M^*$ is the desired carbon source (e.g. methanol) concentration (e.g. grams per liter) in the culture medium (i.e. the set point for the carbon source)

$M^i$ is the concentration (e.g. grams per liter) of the carbon source (e.g. methanol) in the carbon source feed stream OTR is the measured oxygen transfer rate (e.g. grams per liter per hour)

$\tau_d$ is a predetermined time constant associated with the desired response time (e.g. 0.1 hours)

$k^1$ is the ratio of the amount of carbon source consumed to the amount of oxygen consumed (e.g. grams of methanol/grams of oxygen)

V is the liquid volume of the liquid culture medium (e.g. liters).

The above control formula needs the measured value of the variable (i.e. carbon source such as methanol) to be controlled and also the measured value of the oxygen transfer rate (OTR). The OTR variable is an indicator of the biological activity in the fermentor; the OTR value(s) may, for example, be obtained by measuring oxygen in the exhaust gases using appropriate equipment such as "a paramagnetic analyzer" (e.g. from Servomex, France, model 1184) and making the appropriate calculations. The term comprising the OTR variable (i.e. $k^1 * OTR$ as divided by the denominator) will increase in response to the increase in the concentration of the biomass, thus providing a base profile with respect to the carbon source feed rate. The other term $(1/\tau_d) * (M^* - M)$ (again as divided by the denominator) provides for an adjustment around the base profile such that the variable being controlled is maintained at the desired level (i.e. at the set point value).

As mentioned above, the parameter $k^1$ corresponds to the ratio of the amount of carbon source (e.g. methanol) consumed to the amount of oxygen consumed. The above control formula needs the values of this and other parameters. It can be difficult to obtain a good estimate of such values; even worse, they may change during the course of the process. Adaptive control formulae for providing real time estimates of the needed parameters are known for meeting this problem. However, the present invention provides real time estimation formulae (i.e. recursive estimation equations (Ib) and (Ic) as shown below) for providing a real time estimation of the values of certain needed parameters and for allowing for the tracking of any change in these values during the fermentation. Thus the parameter $k^1$ for equation (Ia) is obtained (for a desired point in time) using the equation (Ib)

$$k_t^1 = k_{t-1}^1 - \frac{(1-p)^2 * (M_{t-1} - M'_{t-1})}{T * OTR_{t-1}} \qquad \text{(Ib)}$$

wherein

M' is the calculated carbon source (e.g. methanol) concentration (e.g. grams per liter) in the culture medium obtained using equation (Ic) below T denotes a predetermined sampling time period (i.e. the time period between successive concentration measurements, e.g. 0.008 hours between each methanol concentration measurement)

p denotes a predetermined tuning (adjustment) parameter t is a subscript which characterizes a parameter as denoting a (new) value thereof at the end of the sample period T t-1 characterizes a parameter as denoting the (previous) value of that parameter at the beginning of the sample period T and $k^1$, OTR and M are as defined above; and the parameter M' for equation (Ib) is obtained (for a desired point in time) using equation (Ic)

$$i\, M'_t = M'_{t-1} + x - y + z \qquad \text{(Ic)}$$

wherein x is the term $T*(F/V)_{t-1}*(M^i - M_{t-1})$ y is the term $T*k^1_{t-1}* OTR_{t-1}$ z is the term $2*(1-p)*(M_{t-1}-M'_{t-1})$ $k^1$ is the ratio obtained from equation (Ib) above (for a desired point in time) and T, p, t, t-1, F, OTR, V, M, and $M^i$ are as defined above.

In order to start the equations (Ib) and (Ic) an initial estimated value is provided for the parameters $K^1$ and M', i.e. in addition to the initial values of those parameters which have measurable values; thereafter the equations will generate the necessary values. These equations, preferably, are, of course, rendered into a suitable machine readable form (i.e. a computer program) for use by a computer which is attached in any suitable (known) manner to a means for controlling the methanol additions to the culture medium.

The present invention also provides a means, in the form of the following control equation (IIa) below, for controlling the dissolved oxygen level, i.e. by controlling the agitation speed of the agitator of the fermentation system. The control equation (IIa) takes the following form $$RPM = \frac{((1/\tau_{d3}) * (C^* - C)) + (k^4 * OTR)}{k^5 * (C_s - C)} \quad \text{(IIa)}$$

wherein

RPM is the agitation speed of the system agitator (e.g. revolutions per minute)

C is the measured dissolved oxygen concentration (e.g. grams per liter) in the culture medium $C^*$ is the desired dissolved oxygen concentration (e.g. grams per liter) in the culture medium (i.e. the set point for the dissolved oxygen)

$C_s$ is the dissolved oxygen concentration at liquid saturation i.e. for the liquid culture medium (e.g. g/L)

$\tau_{d3}$ is a predetermined time constant associated with the desired response time (e.g. 0.1 hours)

$k^4$ is a predetermined process parameter $k^5$ is process parameter reflecting the effect of agitation speed on oxygen transfer rate (per rpm per hour)

and OTR is as defined above with respect to the equations (Ia), (Ib) and (Ic).

The present invention further provides real time estimation formulae (i.e. recursive estimation formulae (IIb) and (IIc) as shown below) for providing a real time estimation of the values of certain needed parameters and for allowing for the tracking of any change in these values during the fermentation. Thus the parameter $k^5$ for equation (IIa) is obtained (for a desired point in time) using the equation (IIb)

$$k_t^5 = k_{t-1}^5 + \frac{(1-p_3)^2 * (C_{t-1} - C'_{t-1})}{T * RPM_{t-1} * (C_s - C_{t-1})} \quad \text{(IIb)}$$

wherein

C" is the calculated dissolved oxygen concentration (e.g. grams per liter) in the culture medium obtained using equation (IIc) below T denotes a predetermined sampling time period (i.e. the time period between successive concentration measurements, e.g. 0.008 hours between each methanol concentration measurement)

$P_3$ denotes a predetermined tuning (adjustment) parameter and t, t-1, $k^5$ RPM C and $C_s$ are as defined above; and the parameter C" for equation (IIb) is obtained (for a desired point in time) using equation (IIc)

$$C''_t = C''_{t-1} + x'' + y'' + z'' \quad \text{(IIc)}$$

wherein $x''$ is the term $T*k^5_{t-1}*RPM* (C_s-C_{t-1})$ $y''$ is the term $T* k^{4}* OTR_{t-1}$ $z''$ is the term $2* (1-p_3)*(C_{t-1}-C''_{t-1})$ $k^5$ is the ratio obtained from equation (IIb) above (i.e. for a desired point in time)

and

C, $C_s$, $k^4$, T, $p_3$, t, t-1, and OTR are as defined above.

The present invention also provides an alternative means, in the form of the following control equation (IIIa) below, for controlling the oxygen demand of the fermentation system during that part of the fermentation period when the oxygen demand of the biomass would, if left unchecked, exceed the maximum oxygen transfer rate of the fermentation system; in this case the oxygen requirement of the biomass may be regulated by controlling the carbon source (e.g. methanol) feed rate in response to the dissolved oxygen level. The control equation (IIIa) takes the following form $$F = V* \left[ \frac{((1/\tau_{d2}) * (C^* - C)) + k^2 * OTR}{(k_3 * M^i + C)} \right] \quad \text{(IIIa)}$$

wherein

C is the measured dissolved oxygen concentration (e.g. grams per liter) in the culture medium $C^*$ is the desired dissolved oxygen concentration (e.g. grams per liter) in the culture medium (i.e. the set point for the dissolved oxygen)

$\tau_{d2}$ is a predetermined time constant associated with the desired response time (e.g. 0.1 hours)

$k^2$ is a predetermined process parameter $k^3$ is the (predetermined) ratio of the amount of oxygen consumed to the amount of carbon source consumed (e.g. grams of oxygen/grams of methanol)

and F, OTR, $M^i$ and V are as defined above with respect to the equations (Ia), (Ib) and (Ic).

The present invention further provides real time estimation formulae (i.e. recursive estimation formulae (IIIb) and (IIIc) as shown below) for providing a real time estimation of the values of certain needed parameters and for allowing for the tracking of any change in these values during the fermentation. Thus the parameter $k^2$ for equation (IIIa) is obtained (for a desired point in time) using the equation (IIIb)

$$k_t^2 = k_{t-1}^2 + \frac{(1-p_2)^2 * (C_{t-1} - C_{t-1})}{T * OTR_{t-1}} \quad \text{(IIIb)}$$

wherein

C' is the calculated carbon substrate (e.g. methanol) concentration (e.g. grams per liter) in the culture medium obtained using equation (IIIc) below T denotes a predetermined sampling time period (i.e. the time period between successive concentration measurements, e.g. 0.008 hours between each methanol concentration measurement)

$P_2$ denotes a predetermined tuning (adjustment) parameter and t, t−1, $k^2$, C and OTR are as defined above;

and the parameter C' for equation (IIIb) is obtained (for a desired point in time) using equation (IIIc)

$$C_t = C_{t-1} + x' + y' + z' \quad \text{(IIIc)}$$

wherein
$x'$ is the term $T*(F/V)_{t-1}*(k^3*M^i - C_{t-1})$
$y'$ is the term $T*k^2_{t-1}*OTR_{t-1}$
$z'$ is the term $2*(1-p_2)*(C_{t-1} - C'_{t-1})$
$k^2$ is the ratio obtained from equation (IIIb) above (i.e. for a desired point in time)
and
$C'$, $k^3$, $T$, $p_2$, $t$, $t-1$, $F$, $OTR$, $V$, $C$, and $M^i$ are as defined above.

In the three control equations (eq. Ia, IIa, IIIa), the tuning parameters ($\tau_d$, $\tau_{d2}$ and $\tau_{d3}$) are the time constants of the desired first order linear response. The selection of these desired time constants is done accordingly to the dominant time constant of the process: a too low desired time constant (corresponding to a faster response) might lead to process instabilities. This selection has to be done according to the desires of the user. The tuning parameters (p, $p_2$, and $p_3$) of the recursive estimation algorithms (eq. Ib, Ic, IIb, IIc, IIIb and IIIc) correspond to a pole position in the discrete complex plane and, by this way, are related to the time constant of the estimation dynamics. The value of these parameters has to be between 0 and 1; a value near 0 corresponds to a faster estimation dynamics. Again, the selection of these parameter values depends on desires of the user.

In order to start the equations an initial (i.e. predetermined) estimated value is provided for the parameters $k^1$, $k^2$ and $k^4$, i.e. in addition to the initial values of those parameters which have measurable values; thereafter the equations will generate the necessary values. The values preferably are chosen so as to avoid long periods before they converge to their real values.

These control equations may be converted into a machine readable program in any suitable fashion so as to permit a computer to control a fermentation system in response to the measured values.

By way of example, in the first part of the fermentation where the oxygen transfer is not limiting, the control equations of group I and group II may used (i.e. equations Ia to IIc). Once the process enters into oxygen transfer limitation, control equations of group III (i.e. equations IIIA, IIIb and IIIc) may be used with a constant maximal RPM value (1200 rpm) and control equations of groups I and II are not used any more.

The microorganism may be cultured at any desired temperature keeping in mind that the purpose of the process is to arrive at an end product having a desirable amount of accumulated PHB of desirable quality. The microorganism of the present invention is preferably cultured at a temperature in the range of from about 20 to 40 degrees centigrade e.g. from 28 to 30 degrees centigrade, in particular at about 30° C.

In accordance with the present invention, the microorganism herein may, for example, be cultured aerobically at a dissolved oxygen level of from about 10 to about 15% saturation or more (at atmospheric pressure), preferably at 25% saturation; higher dissolved oxygen levels may, however, be used such as from 20 to about 100 percent air saturation.

The pH of the aqueous medium is to be maintained at a level which facilities the growth of the cells and the production of PHB. The pH may, for example, be in the range of about 6 to about 8, preferably 6.5 to 7. The pH may be controlled in any known manner such as by the addition of small amounts of an acceptable base. Thus as mentioned above, ammonium may be used to control the pH except during a nitrogen starvation phase in which case pH may be controlled by the addition of a non-nitrogenous base such as for example KOH, NaOH, and the like.

The present invention may be used for the production of PHB in high yields and concentrations. It may also provide for a PHB yield of good quality, one measure of which is a high molecular mass value; in general, the higher the molecular mass value the higher the quality of PHB. The degree of polymerization of the PHB chains influences the physical characteristics of the polymer (Lafferty et al., (1988), "Microbial Production of Poly-$\beta$-hydroxybutyric acid", in: Biotechnology, Volume 6B, Chapter 6, edited by: H.-J. Rehm and G. Reed, VCH Verlagsgesellshcaft, mbH, Germany").: the tensile strength increases with molecular mass (weight) (Reymann et al., (1990), "Manufacture of containers from an oriented biopolymer", Technische Mitteilungen Krupp, Number 2 pages 113–118) as well as thermal properties of bacterial poly(D-(−)-$\beta$-hydroxybutyrate", *Int. J. Biol. Macromol.*, volume 10, number 6, pages 373–377). The *Methylobacterium extorguens* strain of the present invention is able to produce PHB with molecular mass values of 1 000 000 Da, or higher, (e.g. a molecular mass of from 100,000 to 2,000,000; in particular from 1,000,000 to 1,800,000 Da) provided appropriate conditions are respected, e.g. with respect to the assimilable nitrogen available, the pH, the methanol concentration and the dissolved oxygen level, etc.; for example, the dissolved oxygen concentration during cultivation may be maintained at from about 10% to 40% oxygen saturation, preferably at 25% oxygen saturation, especially during the second phase favouring PHB production and accumulation.

It is common to in the fermentation art to initiate a given fermentation in a batch mode, this mode being pursued for some hours or days, before switching to a fed-batch mode once a certain appreciable cell density has been reached. One particular advantage of the present invention is that the (control) equations described herein may be used for developing control algorithms which allow for the use of the fed-batch mode right from the beginning, i.e., right after inoculation of the culture medium containing a very low biomass concentration. A fed-batch mode of nutrient addition performs very well even with very dilute microorganism suspensions, as found usually when very small inoculums are used to initiate the fermentation.

In accordance with the present invention pure methanol, may if desired, be added (e.g. in small aliquots) directly to the culture medium during cultivation provided that the addition rate is such as to facilitate and not inhibit the metabolism of microorganisms, i.e. it does not render the medium toxic to the microorganisms. The use of pure methanol obviates the need to add undesirable amounts of water to the bioreactor, so that equipment volume can be reduced and higher biomass and PHB concentrations be reached.

As mentioned above PHB is found within microorganism cells as intracellular granules. In order to purify this PHB, it is thus necessary to extract PHB from the cells. Once extracted, PHB must also be purified. PHB purification may be accomplished using a solvent extraction techniques. Various techniques are known which may be used to accomplish this type of extraction and purification; see for example European patent application no. 8030043;2.4; Berger et al., (1989), "PHB recovery by hypochlorite digestion of non-PHB biomass", Biotechnology Techniques, volume 3, number 4, pages 227-232; Bourque et al., (April, 1992), "Production of poly-β-hydroxybutyrate from methanol: characterization of a new isolate of *Methylobacterium extorguens*", Appl. Microbiol. Biotechnol., volume 37, pages 7-12, etc..

The amount of PHB present in the cells may also be quantified using known techniques; see, for example, Braunegg et al., (1978), "A rapid gas chromatographic method for the determination of poly-β-hydroxybutyric acid in microbial biomass", *Eur. J. Appl. Microbiol. Biotechnol.*, volume 6, pages 29-37, and Bourque et al., (April, 1992), "Production of poly-β-hydroxybutyrate from methanol: characterization of a new isolate of *Methylobacterium extorguens*", Appl. Microbiol. Biotechnol., volume 37, pages 7-12, etc..

Once extracted and purified, the average molecular mass (molecular weight) of the obtained PHB may be determined in known manner; e.g. by viscometric methods, gel permeation chromatographic methods as described by Bourque et al., (April, 1992), "Production of poly-β-hydroxybutyrate from methanol: characterization of a new isolate of *Methylobacterium extorguens*", Appl. Microbiol. Biotechnol., volume 37, pages 7-12.

After extraction of the PHB, the bacterial cell residue may be used as a source of pigments, protein, or cofactors. The residue may also be used as a culture base for other fermentation processes.

Example embodiments of the present invention are illustrated in the following examples.

The fermentor (i.e. bioreactor) used in the following examples were as follows:

3.5 Liter or 14 Liter (theoretical capacity, Model GS (half stainless steel, half glass) bioreactors manufactured and sold by CHEMAP AG (Volketswil, Switzerland). Each of the fermentors was equipped with a pH electrode and a pO2 (dissolved oxygen) electrode, both from Ingold Electrodes Inc. (Wilmington, Mass., U.S.A.). Each of the fermentors was also equipped with a mechanical foam breaker (Model Fundafoam TM) and a foam measuring device, both from CHEMAP AG (address as above). Each of the fermentors was installed on a CHEMAP AG base (Model CF 2000) and controlled using a CHEMAP AG control cabinet (Model FZ-2000).

The variables for the following examples were manipulated as follows:

Example 1: No automatic control

Examples 2 and 3: Control equations of group I during the whole fermentation

Examples 4 and 5: Control equations of groups I, II and III were used; in the first part of the fermentation where the oxygen transfer is not limiting, control equations of groups I and II were used; once the process entered into oxygen transfer limitation (the agitator rpm reached 1200), control equations of group III were used with a constant maximal RPM value (1200 rpm) and control equations I and II were no longer used.

The following values for various parameters for the control equations were used

Equations Ia, 1b, IC (F vs M).

T=0.0083 h $\tau_d$=0.1 h (tuning parameter)

p=0.95 (tuning parameter)

$k^1$ (t=0)=0.5 g/g (initial guess based on average value observed in prior experiments)

Equation IIa, IIb, IIc (RPM vs C)

T=0.0014 h $\tau_{d3}$ =0.000025 h (tuning parameter)

$P_3$=0.75 (tuning parameter)

$C_s$=0.01 g/L $k^4$=−1

$k^5$ (t=0)=0.6 1/rpm/h (initial guess)

Equation IIIa, IIIb, IIIc (F vs C)

T=0.0083

$\tau_{d2}$=0.0025 h (tuning parameter)

$P_2$=0.8 (tuning parameter)

$k^2$ (t=0)=0.8 (initial guess based on average value observed in prior experiments)

$k^3$=−0.5 g/g (based on average value observed in prior experiment)

Note: Selection of tuning parameter is based on prior experimental performance observations.

EXAMPLE 1

Growth of M. extorguens and production of PHB with no intentionally imposed nutritional limitation An inoculum of the *Methylobacterium extorguens* strain is grown aerobically in 500 mL Erlenmeyer flasks containing 100 mL of minimal Medium 784 (see Table 2 above) plus methanol at 1.5% (v/v) (initial concentration). Initial pH of the complete medium was 6.8-7. The culture was incubated at 30° C. for 96 hours at an agitation rate of 250 rpm in a New Brunswick (Model G25) incubator-shaker. Aeration was provided by the good mixing conditions as well known by people in the art of microbial fermentation.

100 mL of the resulting inoculum culture was then added to a bioreactor (3.5 L, theoretical capacity, CHEMAP bioreactor) containing 1.6 L of the Medium 784 but with an initial methanol concentration of 1% (v/v). The bioreactor was of the continuously stirred type, was equipped with a pH electrode and a dissolved oxygen electrode, with a pH controller for continuous adjustment of the pH at a set value, and with a foam sensor device coupled to a mechanical foam breaker for foam control (see above).

The fermentation was carried out at 30° C in a fed-batch mode using the following conditions:

(a) aeration rate (air) at 0.5 vvm, the air being obtained from a central compressor and the volume of air added being controlled by a valve and measured using a rotameter; at the same time, the dissolved oxygen level (pO2 level) was regulated at 65% saturation with the help of the air control valve;

(b) pH was controlled at a value of 6.5 using in KOH added as needed in response to the acidification of the culture medium due to microbial metabolism and measured using a pH electrode;

(c) methanol was added periodically from a methanol reservoir with the help of a pump controlled by a timer (15 mls methanol, 3 times);

(d) ammonium sulfate, the source of nitrogen and sulfur in this experiment, was also added periodically (enough was added to give a final concentration equivalent to that present in the original medium - done three times);

(e) the agitation rate of the agitator was set at 300 rpm;

(f) chemical analysis indicated that it was unlikely that the culture ran out of methanol or of ammonium nitrogen.

The fermentation was stopped at 96 hours and gave the following results: cell biomass concentration, 2.8 g/L (dry weight); PHB concentration: 32% of cell biomass, on a dry weight basis.

EXAMPLE 2

Growth of M. extorguens and production of PHB with intentionally imposed nutritional limitation, i.e., nitrogen limitation An inoculum of the *Methylobacterium extorguens* strain is grown aerobically in 2L Erlenmeyer flasks each containing 500 mL of the minimal medium A1 described in Table 2 above and containing 1% (v/v) methanol at inoculation time. The flasks were incubated at 30° C. for 72 hours at an agitation rate of 250 rpm. Aeration was provided by the good mixing conditions used as done in Example 1.

1000 mL (i.e., the contents of two above flasks) of the resulting inoculum culture was then added to a 14L bioreactor (14 L theoretical capacity, CHEMAP bioreactor, of the continuously stirred type, equipped as described in Example 1). Prior to the addition of the inoculum culture, the bioreactor contained 4 L of the same minimal medium A1 used for inoculum preparation but the medium did not contain any methanol: the methanol content of the resulting mixture, after inoculation, was due to the methanol carried over by the inoculum preparation added to the bioreactor.

The fermentation was carried out at 30° C. in a fed-batch mode under the following conditions:

(a) aeration rate, 10 L (air)/minute, the air being obtained from a central compressor and provided to the culture as described otherwise in Example 1;

(b) the pH was maintained at 7 using concentrated ammonium hydroxide for the first 70 hours then 5N KOH was used thereafter until the end of the fermentation run, i.e. for an additional 26 hours; during the course of the fermentation, ammonium hydroxide or KOH was added as needed in response to the medium acidification caused by microbial metabolism and measured using the pH electrode;

(c) a nonspecific semi-conductor sensor (Figaro TGS 822 as described above) was installed to measure methanol concentration in the exhaust gas; this sensor sent a signal to a computer which controlled a variable rate pump coupled to the methanol reservoir, to start or to stop adding methanol in response to the methanol concentration detected by the methanol sensor used.; during the first 21 hours or so, the methanol reservoir contained a dilute (aqueous) methanol solution (1/6 dilution compared to pure methanol); thereafter, pure methanol was used;

(d) in order to provide the necessary oxygen to the growing culture, the agitation rate of the agitator was gradually increased manually (from 500 rpm) as a means to increase oxygen solubility, and then availability, to the growing culture until a maximal agitation rate of 1200 rpm was reached;

(e) as a means of monitoring the culture conditions, the concentration of $CO_2$ and oxygen in the exhaust gases was continuously monitored using the appropriate equipments "a paramagnetic analyzer" (from Sevomex, France, model 1184) in the case of oxygen and an "infrared $CO_2$ gas analyzer" in the case of $CO_2$: the data collected were then used to calculate the oxygen transfer rate (OTR) and the carbon dioxide transfer rate (CTR), as done by people knowledgeable in the art; when the calculated OTR and CTR values indicated a decrease in metabolic activity, as indicated by a decrease in the calculated values for OTR and CTR, this was taken as a sign of nutrient deficiency and several individual salt solutions; for instance, solutions of ferric sulfate, manganese sulfate, and magnesium sulfate, were serially added to the culture to correct for a possible mineral deficiency; following the addition of the three individual salt solutions, each individual salt being added to give a final concentration equivalent to half the concentration present in the initial culture medium, the new OTR and CTR calculated values indicated an appreciable reactivation of respiratory metabolism.

The fermentation was stopped at around 96 hours.

For determining the percentage of PHB accumulation and the molecular mass (or molecular weight) of the PHB produced, the method of Berger et al (1989) was essentially employed: Berger et al (1989), "PHB recovery by hypochlorite digestion of non-PHB biomass", Biotechnology Techniques, volume 3, No 4, pages 227-232. In our case, methanol, rather than acetone, was used for the initial extraction. About 5 g of lyophilized cells of *M. extorguens* were mixed with 50 mL of methanol and the mixture slowly agitated (150-200 rpm) during 48 hours at a temperature of 30° to 35° C. The cells were thereafter recovered by centrifugation at 4000×g for 10 minutes and mixed with 100 mL of chloroform. The mixture was slowly agitated as previously. The chloroform fraction when then recovered by filtration on Whatman paper No. 1 and evaporated under partial vacuum at 35°-40° C. to give a final volume of 10 to 20 mL.

PHB was then precipitated after the addition of 50 mL of cold ethanol (0° C.); after mixing, the precipitated PHB is recovered by filtration on Whatman paper No.1 and thereafter dried at room temperature under a continuous flow of fresh air. The purified PHB is finally cut into very small pieces and stored at room temperature in a closed container under a dry atmosphere for the further analysis of its molecular mass (weight) value.

In Example 2, the molecular mass of PHB was determined at various times during the production phase. Five PHB samples were analyzed during the period 34 h to 70 h; during this period, the molecular mass of PHB was relatively constant, varying between 127 000 and 157 000 Da. During the period 75 h to 93 h, five other samples were analyzed and indicated that the molecular mass of PHB had increased gradually from 167 500 Da to 341 700 Da. At the end of the fermentation, the cell biomass concentration was 114 g/L (dry weight) and the cells contained 46% PHB on a weight basis.

In Example 2, molecular mass values of PHB produced by *M. extorguens* were determined using a viscosimetric method as described in Bourque et al., (April, 1992), "Production of poly-β-hydroxybutyrate from methanol: characterisation of a new isolate of *Methylobacterium extorguens*, Appl. Microbiol. Biotechnol., volume 37, pages 7–12". The relative viscosimetric shear rate of solutions (in chloroform) containing increasing concentrations of PHB (0.025 to 0.5%, w/v) was determined at 30 +−° C. using a rotational rheometer (Contraves, Zurich, Switzerland; model Low Shear 3). The shear rates used varied from 0 to 100 per second. The intrinsic viscosity (n) was calculated using the equation of Huggins as found in Marchessault et al (1970), "Physical properties of poly ($\mu$-hydroxybutyrate). II Conformational aspects in solution", Macromolecules, volume 3, pages 735–740. Molecular mass was calculated using the Mark-Houwink equation, and the values for the constants K and a were those of Akita et al, (1976), "Solution properties of poly(D-β-hydroxybutyrate) I Biosynthesis and characterization", Macromolecules, volume 9, pages 774–780, and of Marchessault et al (1970) (same reference as above).

People in the art use generally the expression "molecular weight" with respect to the PHB polymer chains (examples: Lafferty, et al (1988) Biotechnology, volume 6B, chapter 6, edited by R.-J. Rehm ad G. Reed VCH; Berger et al (1989) "Hypochlorite digestion of non-PHB biomass", Biotechnology Techniques, volume 3, number 4, pages 227–232; Anderson and Dawes, (1990), "Occurrence, metabolism, metabolic role, and industrial uses of bacterial polyhydroxyalkanoates", Microbiological Rev, volume 54, No. 4, pages 350–472; Suzuki et al, (1986), "Mass production of poly-β-hydroxybutyric acid by fully automatic fed-batch cult ure of methylotroph", Appl. Microbiol. Biotechnol., volume 23, pages 322–329). Recently, the expression "molecular mass" has been used in replacement of "molecular weight" (i.e. expressed as Da=Daltons) with respect to the PHB polymer chains (Bourque et al, (1992), "Production of poly-β-hydroxybutyrate from methanol: characterization of a new isolate of *Methylobacterium extorguens*", Appl. Micriobiol. Biotechnol., volume 37, pages 7–12).

EXAMPLE 3

Growth of *Methylobacterium extorguens* using some mineral supplementation during the phase of biomass production and an intentionally imposed nitrogen limitation during the PHB accumulation phase.

An inoculum of the new *Methylobacterium extorguens* strain was grown aerobically in the same minimal medium used for inoculum preparation in Example 2 except that 500 mL Erlenmeyer flasks containing 200 mL of the culture medium (initial methanol concentration: 1%(v/v)) were used. Other conditions for inoculum preparation were the same as described in Example 2. 500 mL (the contents of 1 above flask) of the resulting inoculum culture was then added to a 3.5 L bioreactor (the same bioreactor described in Example 1) containing 800 mL of the same minimal medium used for inoculum preparation except for the absence of methanol.

The fermentation was carried out in a fed-batch mode under the following conditions:
 (a) 30° C;
 (b) aeration, 10L (air)/min, carried out as otherwise described in Example 1;
 (c) pH controlled at 7.0 using concentrated ammonium hydroxide (dilution ½) for the first 70 hours or so, thereafter using 5N KOH for the remaining fermentation period, i.e. for the remaining 23.5 hours;
 (d) methanol addition to the culture was done as described in Example 2 using the same control system;
 (e) contrary to Example 2, however, the methanol reservoir contained methanol diluted 1/5 (v/v) with water and this mixture also contained some minerals such as phosphoric acid, magnesium sulfate, calcium chloride and ferric sulfate; in the present example, the final concentration of each of these minerals was as follows (per 100 mL of the diluted methanol solution): phosphoric acid, 0.47 g; magnesium sulfate ($MgSO_4.7H_2O$), 0.69 g; calcium chloride ($CaCl_2.2H_2O$), 0.03 g; ferric sulfate ($FeSO_4.7H_2O$), 0.04 g; this methanol-salt mixture was used as carbon and mineral feed for the first 27 hours of the fermentation; (f) from 27 h to the end of the methanol fermentation, pure methanol was used as carbon and energy source; the control of methanol addition to the culture, and the maintenance of the methanol concentration at the desired value in the culture medium was performed as described for Example 2;
 (g) in order to Supply the necessary quantities of oxygen to the aerobic microorganism, the agitation rate of the agitator was gradually and manually increased from 400 to 1000 rpm; it is well known that increasing agitation rate increases oxygen dissolution into the culture medium.

The fermentation was carried out for 93.5 hours. At this time, samples of the culture were analyzed for cell biomass and PHB content and for PHB quality (molecular mass value). All analyses were carried out as described in Example 2. At 93.5 h, the culture contained 95.8 g/L of dry cell biomass containing 40.1% of PHB (on the basis of dry weight). The PHB showed a molecular mass value of 300 000 Da.

EXAMPLE 4

Growth of *Methylobacterium extorguens* and production of PHB using an intentionally imposed nitrogen limitation: Control of the methanol concentration in the liquid culture medium at two different concentrations and use of a chemical antifoam.

An inoculum of the new *Methylobacterium extorguens* strain is grown aerobically in 2 L Erlenmeyer flasks containing 500 mL of a minimal medium (Medium A1) described in Table 2 above and containing 1% (v/v) methanol at inoculation time. The culture was incubated aerobically at 30° C. for 72 hours at an agitation rate of 250 rpm as done in previous Examples.

500 mL (the contents of 1 above flask) of the resulting inoculum culture was then added to a 14 L bioreactor containing 4.5 L of the minimal culture Medium A2 as described in Table 1 above. The bioreactor and all other peripheral equipments needed were the same as used in Example 2. The culture medium used, i.e. Medium A2 in Table 1, was a slight modification of the culture medium (Medium A1 above) used for inoculum preparation; as done in Example 2, the culture medium present initially in the bioreactor did not contain any methanol, and the methanol possibly present in the culture medium right after inoculation was due to the methanol carried over by the inoculum preparation added to the bioreactor.

The fermentation was performed in a fed-batch mode under the following conditions:
(a) 30° C.;
(b) aeration at 10 L (air)/min, the air being provided by a central compressor and its addition being controlled by a valve and measured via a rotameter; in this experiment, once the dissolved oxygen level (pO2) was naturally lowered to 25% saturation (at atmospheric pressure) due to consumption by the bacteria, the level of dissolved oxygen (pO2) was successfully maintained at 25% saturation (at atmospheric pressure) as described below;
(c) pH was maintained at 7 using concentrated ammonium hydroxide diluted ¼ for the first 27 hours, then using a ½ dilution, for the next 23 hours, and finally 5N KOH was used from 50 h to the end of the fermentation, i.e. for the remaining 17.8 hours; as in previous Examples, the addition of the appropriate alkaline solution was done in response to the acidification of the culture medium caused by microbial metabolism and measured by the pH electrode;
(d) control of the methanol concentration: this time, the sensor was set up in such a way that it measured the concentration of methanol in the liquid phase rather than in the exhaust phase as done previously; here, a semi-conductor sensor, namely a Figaro TGS 812, as mentioned earlier; overall, the fermentation was carried out in three distinct phases as follows: (1) for the first 15 hours, the concentration of methanol was maintained at 1.4 g/L (agitation rate fixed at 500 rpm) and dissolved oxygen level maintained at 25% saturation once it reached this level; at inoculation time, the dissolved oxygen level was about 80–90% of saturation but decreased normally to 25% saturation (the desired set-point value) due to consumption by the bacteria; (2) from 15 h to 21 h, the concentration of methanol was also maintained at 1.4 g/L but the agitation rate was gradually increased from 500 to 1200 rpm (maximum) while the dissolved oxygen level was maintained at 25% saturation; (3) from 21 h until the end, the concentration of methanol was maintained below 0.01 g/L and the agitation rate fixed at 1200 rpm while the dissolved oxygen level was successfully maintained at 25% saturation.

Some chemical antifoam, such as Ucarferm adjuvant 27 (UNION CARBIDE), was used intermittently to control foaming. At 67.8 h, the cell biomass was 89.04 g/L (dry weight) containing 37.5% PHB (dry weight basis). The PHB had a molecular mass value of 1 500 000 Da as determined, in this experiment, by a gel permeation chromatographic method as described by Bourque et al, (1992), "Production of poly-β-hydroxybutyrate from methanol: characterization of a new isolate of *Methylobacterium extorguens*", Appl. Micriobiol. Biotechnol., volume 37, pages 7–12.

EXAMPLE 5

Growth of *Methylobacterium extorguens* and production of PHB using an intentionally imposed nitrogen limitation: Effect of a new chemical antifoam The inoculum was prepared exactly as described in Example 4.

The fermentation was done basically as described in Example 4 except that:
(a) pH was maintained at 7 using concentrated ammonium hydroxide diluted ¼ with water for the first 24 hours then using concentrated ammonium hydroxide diluted ½ with water from 24 h to 47 h. From 47 h until the end of the fermentation (i.e. the remaining 20 hours), 5N KOH was used to control pH; the addition of ammonium hydroxide or of KOH was in direct response to the acidification of the culture medium caused by microbial metabolism and measured by the pH electrode.

As in Example 4, once the dissolved oxygen level was decreased to 25% saturation, due to oxygen consumption by the bacteria, the level of dissolved oxygen was thereafter successfully maintained at 25% saturation (at atmospheric pressure) during the whole fermentation using essentially the same control strategies used and described in Example 4. At various times during the fermentation, the chemical antifoam Struktol DA-673 was used to control foaming: the addition, when needed, of the chemical antifoam was carried out automatically and was under the control of a foam-sensitive probe (sensor) sending a signal to a pump to add chemical antifoam as needed. The chemical antifoam used in this experiment appeared to be partially degraded by the microorganism. All pertinent analyses were performed as described in Example 4. At 47 h, the cell biomass was 53.95 g/L (dry weight) containing 34.3% PHB (w/w) with a molecular mass value of 1 800 000 Da. At 67 h, the cell biomass was 40.6 g/L containing 21.8% of PHB having a molecular mass value of 1 550 000 Da. The chemical antifoam used appeared to be deleterious to the fermentation although it was partially degraded. This deleterious effect manifested itself by a significant decrease in cell biomass production, in PHB accumulation, and in the quality (molecular mass value) of the PHB, as indicated by a comparison of the results obtained at 47 h and 67 h.

We claim:

1. A method of producing a polymer comprising repeating units of formula

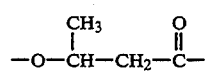

said method comprising aerobically culturing a purified *Methylobacterium extorguens* microorganism strain designated by the ATTC no. 55366 whereby said polymer is accumulated in said microorganism.

2. A method as defined in claim 1 comprising culturing the microorganism on an assimilable carbon source in an aqueous medium.

3. A method as defined in claim 2 wherein the assimilable carbon source comprises methanol.

4. A method as defined in claim 1 comprising culturing the microorganism in a first stage on an assimilable carbon source in an aqueous medium comprising sufficient assimilable nitrogen for microbial growth, and thereafter continuing culturing under nitrogen starvation conditions.

5. A method as defined in claim 4 wherein the assimilable carbon source comprises methanol.

6. A method as defined in claim 5 including the step of recovering the polymer from the microorganism.

7. A method as defined in claim 6 wherein the polymer recovered has a molecular mass of from 100,000 Da to 2,000,000 Da.

8. A method as defined in claim 1 wherein compressed air is used as a source of oxygen for the aerobic cultivation of said microorganism.

9. A method of producing a polyester comprising repeating units of formula

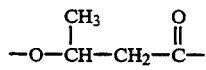

said method comprising aerobically culturing a microorganism, capable of accumulating said polyester, in an aqueous medium on an assimilable carbon source consisting of methanol, with at least part of the cultivation being conducted under a starvation condition whereby one or more essential requirements for microbial growth is limited and whereby said polyester is accumulated in said microorganism, characterized in that said microorganism consists of a purified *Methylobacterium extorguens* microorganism strain designated by the ATTC no. 55366.

10. A method as defined in claim 9 wherein at least part of the cultivation is conducted under a starvation condition whereby assimilable nitrogen is limited.

11. A method as defined in claim 9 including the step of recovering the polyester from the microorganism.

12. A method as defined in claim 11 wherein the polymer recovered has a molecular mass of from 100,000 Da to 2,000,000 Da.

13. A method as defined in claim 12 wherein compressed air is used as a source of oxygen for the aerobic cultivation of said microorganism.

14. A method as defined in claim 9 wherein the starvation condition is imposed when the microorganism cell mass is, on a dry weight basis, 20 g/l or more.

15. A method as defined in claim 9 wherein the starvation condition is imposed when the microorganism cell mass is, on a dry weight basis, in the range of from 20 g/l to 90 g/l.

16. A method as defined in claim 4 wherein the culturing includes pH control, wherein during the first stage the pH of the culture is controlled by the addition of a base comprising assimilable nitrogen and during the second stage the pH is controlled by the addition of a base which does not comprise assimilable nitrogen.

17. A method as defined in claim 16 wherein the base comprising assimilable nitrogen is $NH_4OH$ and the non-nitrogenous base is KOH.

18. A method of producing a polymer comprising repeating units of formula

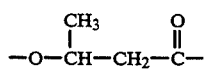

wherein a purified *Methylohacterium extorguens* microorganism strain designated by the ATTC no. 55366 is aerobically cultivated in an aqueous medium on an assimilable carbon source, whereby said polymer is accumulated in said microorganism, characterized in that said method comprises the step of adding said carbon source to the aqueous medium in accordance with the following equation (Ia)

$$F = V * \left[ \frac{((1/\tau_d) * (M^* - M)) + (k^1 * OTR)}{(M^i - M)} \right] \quad \text{(Ia)}$$

wherein

F is the feed rate of the carbon source feed stream

M is the measured concentration of the carbon source in the aqueous medium $M^*$ is the desired carbon source concentration in the aqueous medium $M^i$ is the concentration of the carbon source in the carbon source feed stream OTR is the measured oxygen transfer rate $\tau_d$ is a predetermined time constant $k^1$ is the ratio of the amount of carbon source consumed to the amount of oxygen consumed V is the liquid volume of the aqueous medium and wherein $k^1$ is determined in accordance with equation (Ib)

$$k_t^1 = k_{t-1}^1 - \frac{(1-p)^2 * (M_{t-1} - M'_{t-1})}{T * OTR_{t-1}} \quad \text{(Ib)}$$

wherein

T denotes a predetermined sampling time period for the measured parameters M and OTR, p denotes a predetermined tuning parameter t is a subscript which characterizes a parameter as denoting a value thereof at the end of the sample period T t-1 characterizes a parameter as denoting the value of that parameter at the beginning of the sample period T and $k^1$, OTR and M are as defined above, and wherein M' is the calculated carbon source concentration in the aqueous medium as determined in accordance with equation (Ic)

$$M'_t = M'_{t-1} + x - y + z \quad \text{(Ic)}$$

wherein x is the term $T*(F/V)_{t-1}*(M^i - M_{t-1})$ y is the term $T*k^1_{t-1}* OTR_{t-1}$ z is the term $2*(1-p)*(M_{t-1} - M'_{t-1})$ $k^1$ is determined in accordance with equation (Ib) above and T, p, t, t-1, F, OTR, V, M, and $M^i$ are as defined above.

19. A method of producing a polymer comprising repeating units of formula

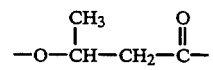

wherein a purified *Methylobacterium extorguens* microorganism strain designated by the ATTC no. 55366 is aerobically cultivated in an aqueous medium on an assimilable carbon source, whereby said polymer is accumulated in said microorganism, characterized in that said method comprises the step of adding said carbon source to the aqueous medium in accordance with the following equation (IIIa)

$$F = V * \left[ \frac{((1/\tau_{d2}) * (C^* - C)) + k^2 * OTR}{(k_3 * M^i + C)} \right] \quad \text{(IIIa)}$$

wherein

F is the feed rate of the carbon source feed stream $M^i$ is the concentration of the carbon source in the carbon source feed stream OTR is the measured oxygen transfer rate V is the liquid volume of the aqueous medium C is the measured dissolved oxygen concentration in the aqueous medium C* is the desired dissolved oxygen concentration in the aqueous medium $\tau_{d2}$ is a predetermined time constant $k^2$ is a predetermined process parameter $k^3$ is the ratio of the amount of oxygen consumed to the amount of carbon source consumed and wherein $k^2$ is determined in accordance with equation (IIIb)

$$k_t^2 = k_{t-1}^2 + \frac{(1-p_2)^2 * (C_{t-1} - C'_{t-1})}{T * OTR_{t-1}} \quad \text{(IIIb)}$$

wherein
T denotes a predetermined sampling time period
$P_2$ denotes a predetermined tuning parameter and t, t-1, $k^2$, C and OTR are as defined above; and wherein C' is the calculated dissolved oxygen concentration in the aqueous medium as determined in accordance with equation (IIIc)

$$C'_t = C_{t-1} + x' + y' + z' \quad \text{(IIIc)}$$

wherein
x' is the term $T*(F/V)_{t-1}*(k^3*M^i - C_{t-1})$
y' is the term $T, k^z * OTR_{t-1}$
z' is the term $2*(1-p_2)*(C_{t-1} - C'_{t-1})$
$k^2$ is the ratio obtained from equation (IIb) above and C', $k_3$, T, $p_2$, t, t-1, F, OTR, V, C, and $M^i$ are as defined above.

* * * * *